(12) United States Patent
Kim et al.

(10) Patent No.: US 9,833,464 B2
(45) Date of Patent: Dec. 5, 2017

(54) TARGET-AIMING DRUG DELIVERY SYSTEM FOR DIAGNOSIS AND TREATMENT OF CANCER CONTAINING LIPOSOME LABELED WITH PEPTIDES WHICH SPECIFICALLY TARGETS INTERLEUKIN-4 RECEPTORS, AND MANUFACTURING METHOD THEREOF

(75) Inventors: In San Kim, Daegu (KR); Byung Heon Lee, Daegu (KR); Maggie J M Lu, Hsinchu (TW); Hsiang-Fa Liang, Hsinchu (TW); Yi-ju Ko, Xinbei (TW); Ya-Chin Lo, Taichung (TW); Li-Wen Chang, Hsinchu (TW); Ming-Cheng Wei, Taoyuan (TW)

(73) Assignees: KYUNGPOOK NATIONAL UNIVERSITY INDUSTRY-ACADEMIC COOPERATION FOUNDATION, Daegu (KR); INDUSTRIAL TECHNOLOGY RESEARCH INSTITUTE, Hsinchu (TW)

( * ) Notice: Subject to any disclaimer, the term of this patent is extended or adjusted under 35 U.S.C. 154(b) by 1208 days.

(21) Appl. No.: 13/519,821

(22) PCT Filed: Dec. 29, 2010

(86) PCT No.: PCT/KR2010/009495
§ 371 (c)(1),
(2), (4) Date: Jun. 28, 2012

(87) PCT Pub. No.: WO2011/081443
PCT Pub. Date: Jul. 7, 2011

(65) Prior Publication Data
US 2012/0294931 A1    Nov. 22, 2012

(30) Foreign Application Priority Data
Dec. 29, 2009 (TW) .............................. 098145476 A (51) Int. Cl.
| | | |
|---|---|---|
| *A61K 31/70* | (2006.01) | |
| *A61K 31/704* | (2006.01) | |
| *A61K 47/48* | (2006.01) | |
| *A61K 9/127* | (2006.01) | |
| *A61K 38/00* | (2006.01) | |

(52) U.S. Cl.
CPC .......... *A61K 31/704* (2013.01); *A61K 9/1271* (2013.01); *A61K 47/48815* (2013.01); *A61K 38/00* (2013.01)

(58) Field of Classification Search
CPC .................. A61K 31/704; A61K 38/00; A61K 47/48815; A61K 9/1271
See application file for complete search history.

(56) References Cited

U.S. PATENT DOCUMENTS

| | | | |
|---|---|---|---|
| 6,426,086 B1 * | 7/2002 | Papahadjopoulos . | A61K 9/1272 424/1.21 |
| 6,958,241 B2 | 10/2005 | Martin et al. | |
| 7,968,081 B2 | 6/2011 | Lee et al. | |
| 2005/0158375 A1 * | 7/2005 | Kimura ................ | A61K 9/1272 424/450 |
| 2009/0074663 A1 | 3/2009 | Lee et al. | |
| 2009/0291049 A1 | 11/2009 | Nuno Sereno de Almeida Moreira et al. | |
| 2010/0086585 A1 * | 4/2010 | Smith .................. | A61K 9/0019 424/450 |

OTHER PUBLICATIONS

Harasym et al., Advanced Drug Delivery Reviews 32:99-118, 1998.*
Tungekar et al., "Interleukin 4 Receptor Expression on Human Lung Tumors and Normal Lung," Cancer Research, Jan. 1, 1991, vol. 51, pp. 261-264.
Hai-yan Hong et al., "Phage Display Selection of Peptides that Home to Atherosclerotic Plaques: IL-4 Receptor as a Candidate Target in Atherosclerosis," Journal of Cellular and Molecular Medicine, Nov. 2007, Postprint;10.1111/j.1582-4934.2007.00189.x.
Kyeongsoon Park et al, "A new atherosclerotic lesion probe based on hydrophobically modified chitosan nanoparticles functionalized by the atherosclerotic plaque targeted peptides," Journal of Controlled Release, vol. 128, 2008, pp. 217-223.
PCT International Search Report dated Sep. 26, 2011, issued in a corresponding PCT Application No. PCT/KR2010/009495, filed Dec. 29, 2010 (2 pages).
"1999 Fiscal Year Annual Research Report", KAKEN, 1999, 2 pages.

* cited by examiner

*Primary Examiner* — Prema Mertz
(74) *Attorney, Agent, or Firm* — Lucas & Mercanti, LLP (57) ABSTRACT

The present invention relates to a target-aiming drug delivery system for diagnosis and treatment of cancer containing liposome labeled with peptides which specifically targets interleukin-4 receptors, and a manufacturing method thereof. The liposome which contains anticancer drugs labeled with IL4RPep peptides prepared in accordance with the present invention can deliver drugs to cancer cells in which IL-4 receptors are overexpressed by IL4RPep peptides which specifically bind to IL-4 receptors, and the drug delivery can recognize cancer cells specifically by a label. Thus, IL4RPep peptides can increase the effect of drugs only on cancer tissues and at the same time significantly reduce the side effects on normal tissues, which makes possible in vivo(molecular) imaging and early diagnosis of tumors. Therefore, the liposome which contains anticancer drugs labeled with IL4Pep peptides of the present invention can be applied, as the target-aiming drug delivery system, effectively to the diagnosis and treatment of cancers.

7 Claims, 10 Drawing Sheets

TARGET-AIMING DRUG DELIVERY SYSTEM FOR DIAGNOSIS AND TREATMENT OF CANCER CONTAINING LIPOSOME LABELED WITH PEPTIDES WHICH SPECIFICALLY TARGETS INTERLEUKIN-4 RECEPTORS, AND MANUFACTURING METHOD THEREOF

CROSS-REFERENCE TO RELATED APPLICATIONS

This application is a 371 of PCT/KR2010/009495, filed Dec. 29, 2010, which claims the benefit of Taiwanese Patent Application No. 098145476, filed Dec. 29, 2009, the entire contents of each of which are incorporated herein by reference.

TECHNICAL FIELD

The present invention relates to a target-aiming drug delivery system for the diagnosis or treatment of cancer, comprising a liposome labeled with a peptide that specifically targets interleukin-4 receptors, and a method for manufacturing the same.

BACKGROUND ART

Interleukin-4 (IL-4) is a cytokine which has many biological and immunoregulatory functions and is released from T-helper 2 (Th2) lymphocytes, eosinophils, and mast cells. IL-4 receptors are found on normal T lymphocytes, B lymphocytes and CD34 myelocytes (Nelms, Annu Rev Immunol, 1999; 17:701-738 ). A functional IL-4 receptor is composed of two transmembrane proteins. The IL-4Rα chain binds IL-4, leading to dimerization with either the IL-2 receptor gamma chain (γC) or with the IL-13 receptor α1 chain to form the type I or type II receptor complexes, respectively. IL-4 engagement of IL-4R results in the phosphorylation of intracellular Janus kinase. The phosphorylated kinase phosphorylates and activates STAT6, which in turn dimerizes and is subsequently translocated to the nucleus wherein the STAT6 promotes transcription of target genes associated with IL-4, inducing inflammation. In a second way, occupation of the IL-4 receptor by IL-4 induce the Janus kinase-mediated AKT/PKB, resulting in increasing cell survival (Nelms et al., Annu Rev Immunol, 1999; 17:701-738). IL-4 also functions to induce the differentiation of naive T-helper (Th) cells to Th2 lymphocytes and the production of cytokines such as IL-4, IL-5, IL-9 and IL-13. Also, IL-4 induces B-cell class switching to IgE (immunoglobulin E). Particularly, IL-4 is implicated in mucin gene expression and mucous hypersecretion, which are features in the pathogenesis of asthma, thus playing an important role in airway obstruction and inflammation (Paul, Blood, 1991; 77:1859-1870). As such, IL-4 is a key regulator in allergic inflammatory response. Accordingly, the proper inhibition of the functions of IL-4 may be appropriate for the treatment of allergic diseases.

In addition, higher levels of IL-4 are found in various cancer tissues than in normal tissues and it is produced in a large amount in tumor-infiltrating lymphocytes (TILs) (Shurin, Springer Semin Immunopathol, 1999; 21:339). IL-4 endows chronic lymphocytic leukemia B cells with resistance to apoptotic cell death (Dancescu, J Exp Med, 1992; 176:1319). Recent reports have exhibited that IL-4 is synthesized in tumor cells and cancer stem cells and binds to the IL-4 receptor on cancer cells to make the cancer cells resistant to apoptosis (Todaro, Cell Death Differ, 2008; 15:762-772; Todaro, Cell Stem Cell, 2007, 1:389-402). The expression level of IL-4 receptors in various cancer cells including non-small cell lung cancer, encephaloma, breast cancer, bladder cancer, pancreatic cancer, prostate cancer, kidney cancer, and Kaposi's sarcoma is much higher than normal cells. In consideration of the acquisition of anticancer agent resistance thereby and the overexpression thereof in cancer cells, the IL-4 receptor may be a promising target for cancer therapy. A fusion protein in which modified IL-4 is fused to pseudomonas toxin is reported to target cancer cells so that the toxin is introduced into the cancer cells to kill them (Joshi, Cancer Res, 2001: 61:8058-8061; Garland, J Immunother, 2005: 28:376-381; Kioi, Cancer Res, 2005: 65:8388-8396; Kawakami, Clin Cancer Res, 2002:8:3503-3511).

Meanwhile, a variety of IL-4 antagonists have been developed as therapeutics for asthma. For example, Immunex Corp. produced Nuvance™, a soluble form of IL-4 receptor, which advanced to clinical trial, but its development was halted due to insufficient therapeutic effects. Pascolizumab, a monoclonal antibody to IL-4, developed by Glaxosmithkline, underwent a clinical trial, but underwent no further development. Bayer developed Pitrakinra, a dual IL-4/IL-13 antagonist in clinical trial studies for the potential treatment of asthma. Sunesis Pharm. Inc developed triphenyl compounds as IL-4 antagonists in clinical trials (WO 2001/098245).

In conventional chemotherapy, anticancer agents, after being administered orally or by injection, are intended to be maintained at a desired concentration in vivo to exert a pharmaceutical effect on an affected site in need thereof, but they affect normal sites as well, incurring side effects. To overcome this drawback, increasing attention has been paid to a drug delivery system capable of delivering drugs selectively to affected sites, or a target therapy which can increase pharmaceutical efficacy even at low dosages accompanied by the concomitant great decrease of side effects in normal tissue.

Generally, a target-aiming drug delivery system is composed of three parts: a soluble polymeric carrier for carrying a drug; a target moiety for allowing a drug to react with a target site; and a spacer for bio-conjugating the drug to the polymeric carrier. In this structure, the drug delivery system enjoys the advantage of increasing lipid-soluble drugs in water solubility, stabilizing the conformation of protein or peptide drugs and reducing side effects or multidrug resistance for anticancer agents. Particularly, the target moiety guides the selective reaction of the drug with target cells or tissues, so that the system is applicable even to small-size tumors in the early stage, thus effectively treating diseases.

A liposome is a spherical vesicle composed of a lipid bilayer. The lipid bilayer is made mostly of phospholipids which are amphiphilic with a hydrophilic phosphate head and two hydrophobic lipid tails. When exposed to an aqueous phase, phospholipids arrange themselves into a bilayer which may form a closed structure like a cell. In the bilayer structure, the hydrophobic lipid tails face inside with the hydrophilic head facing outside. The major types of liposomes are the multilamellar vesicle and the unilamellar vesicle. Unilamellar liposomes have single lipid bilayers while multilamellar liposomes contain two or more lipid bilayers. Liposomes may be prepared by various methods [Cullis et al., in: Liposomes, From Biophysics to Therapeutics (M. J. Ostro, ed.), Marcel Dekker, pp. 39-72(1987)].

Because they are delivered selectively to an affected site, a drug loaded into a liposome has decreased side effects and increased pharmaceutical efficacy. In addition, liposomes are typically captured by phagocytic cells of the reticuloendothelial system in the capillaries so that the loaded drug is released directly into the intracellular infected site.

An anticancer agent-loaded liposome labeled with an IL-4 receptor-targeting peptide can be used as a drug carrier that delivers the drug selectively to the cancer tissue of interest. Therefore, the IL-4 receptor is thought to be useful as a smart drug carrier for cancer therapy.

DISCLOSURE

Technical Problem

Leading to the present invention, intensive and thorough research into a target-aiming drug delivery system, conducted by the present inventors resulted in the finding that when a peptide that specifically targets the IL-4 receptor is combined with an anticancer agent-loaded liposome, the liposome can deliver the drug selectively to cancer cells on which the IL-4 receptor is overexpressed.

Technical Solution

It is therefore an object of the present invention to provide a target-aiming drug delivery system for the diagnosis or treatment of cancer, comprising a liposome labeled with a peptide that can specifically target the interleukin-4 receptor, and a method for manufacturing the same.

BEST MODE

In accordance with an aspect thereof, the present invention addresses a target-aiming drug delivery system for the diagnosis or treatment of cancer, comprising as an active ingredient an anticancer agent-loaded liposome that is labeled with an interleukin-4 receptor targeting peptide (IL4RPep) having the amino acid sequence of SEQ ID NO: 1, the peptide being present in an amount of 0.1~5 mol % based on the total moles of the lipids of the liposome.

In accordance with another aspect thereof, the present invention provides a method for manufacturing a target-aiming drug delivery system for the diagnosis or treatment of cancer, comprising:

A method for manufacturing a target-aiming drug delivery system for diagnosis or treatment of cancer, comprising:

1) dissolving first lipids, second lipids and cholesterol in ethanol to assure a lipid mixture, hydrating the mixture in water to form a lipid suspension, and forcing the lipid suspension through a filter to yield homogeneous liposomes, 2) loading an anticancer agent into the liposomes formed in step 1) to afford anticancer agent-loaded liposomes, 3) labeling the anticancer agent-loaded liposomes with a marker, and 4) conjugating an IL-4 receptor-targeting peptide (IL4RPep) having the amino acid sequence of SEQ ID NO: 1 to maleimide-modified DSPE-PEG$_{2000}$ (DSPE-PEG$_{2000}$-maleimide) and reacting the conjugate with the anticancer agent-loaded liposome labeled with the marker to insert the IL4RPep into the liposomes.

Below, a detailed description will be given of the present invention.

The target-aiming drug delivery system for the diagnosis or treatment of cancer according to the present invention comprises as an active ingredient an anticancer agent-loaded liposome that is labeled with IL-4 receptor-targeting peptide (IL4RPep) having the amino acid sequence of SEQ ID NO: 1 (CRKRLDRNC), the peptide being present in an amount of 0.1~5 mol % based on total moles of lipid in the liposomes.

The liposomes are multilamella liposomes composed of first lipids, second lipids and cholesterols. Examples of the first lipids include, but are not limited to, phosphatidyl choline (PC), phosphatidyl glycerol (PG), phosphatidyl serine (PS), and phosphatidyl ethanolamine (PE). The first lipids preferably amount to 60~70 mol % of the total lipids in the liposome.

Among the second lipids useful in the present invention is distearoylphosphatidylethanolamine-polyethylenoglycol (DSPE-PEG), but the present invention is not limited to this. Preferably, the second lipids are present in an amount of 1~10 mol % of the total lipids in the liposomes.

The cholesterols are preferably contained in an amount of 1~40 mol % of total lipids in the liposomes.

Examples of the anticancer agent that can be loaded into the liposomes include doxorubicin, paclitaxel, vincristine, daunorubicin, vinblastine, actinomycin-D, docetaxel, etoposide, teniposide, bisantrene, homoharringtonine, Gleevec (STI-571), cisplatin, 5-fluorouracil, adriamycin, methotrexate, busulfan, chlorambucil, cyclophosphamide, melphalan, nitrogen mustard, and nitrosourea, but are not limited thereto.

The cancers to which the drug delivery system is applicable are those on which the IL-4 receptor is overexpressed. Examples of the cancers include lung cancer, encephaloma, breast cancer, liver cancer, skin cancer, esophageal cancer, testis cancer, kidney cancer, large intestine cancer, rectal cancer, stomach cancer, bladder cancer, ovarian cancer, cholangiocarcinoma, gallbladder carcinoma, uterine cancer, uterine cervical cancer, prostate cancer, head and neck cancer, pancreatic cancer, and squamous cell carcinoma, but are not limited thereto.

Below, the method for manufacturing the target-aiming drug delivery system for the diagnosis or treatment of cancer in accordance with the present invention will be explained in detail.

Step 1 is directed to the preparation of liposomes. First lipids, second lipids and cholesterols are dissolved at a molar ratio of 60~70:1~10:1~40 in ethanol at 50~70° C. The resulting lipid mixture is hydrated at a volume ratio of 1:5~15 with water at 50~70° C. The hydrated lipid mixture is forced to pass through a polycarbonate membrane filter with a pore size of 0.01~0.5 μm to yield liposomes that are homogeneous in size. The size of liposomes may be controlled using many known methods.

Preferably, the prepared liposomes are multilamellar liposomes with two or more lipid bilayers. The multilamellar liposomes has a diameter of 5 μm or less, preferably 1 μm or less, more preferably 50~500 nm, and most preferably 80~150 nm.

Step 2 is adopted to load the liposomes with the anticancer agent. After the addition of ammonium sulfate $((NH_4)_2SO_4)$, the aqueous phase of a liposome solution is excluded, liposomes are dialyzed against a sufficient amount of a 10% sucrose buffer containing NaCl to remove ammonium sulfate from the surface of the liposomes. Then, an anticancer agent is added to the liposome solution and incubated at 50~70° C. for 1~3 hours, followed by rapid chilling to load the anticancer agent into the liposomes. In this context, the concentration of the anticancer agent loaded into the liposomes is on the order of 1~5 mg/mL and preferably on the order of 1.5~2 mg/mL. Loading of anticancer agents into liposomes may be implemented using methods known in the art. For example, simple capture or entrapment, covalent bonding, or cross linking may be employed.

In step 3), the anticancer agent-loaded liposomes are labeled with a marker. The marker is adopted to make it easy to identify and quantify the cancer cells targeted by the liposomes. The marker may be attached to the liposomes using a method known in the art. Examples of the marker useful in the art include radioisotopes (e.g., $^{125}I$, $^{32}P$, $^{35}S$), chromophores, luminescent or fluorescents [e.g., FITC, RITC, GFP (green fluorescent protein); EGFP (enhanced green fluorescent protein), RFP (red fluorescent protein); DsRed (Discosoma sp. red fluorescent protein); CFP (cyan fluorescent protein), CGFP (cyan green fluorescent protein), YFP (yellow fluorescent protein), Cy3, Cy5, Cy5.5 and Cy7.5], super paramagnetic particles, ultrasuper paramagnetic particles and chromogenic enzymes (e.g., peroxidase, alkaline phosphatase), but are not limited thereto.

The detection of markers may be conducted using methods known in the art. When a fluorescent compound is used as a detectable marker, an immunofluorescence method may be selected. For example, fluorescent-labeled liposomes are reacted with a sample and the products that stay unbound or are non-specifically bound are removed before observation of liposomal fluorescence under a fluorescence microscope. After a chromogenic enzyme is used as a detectable marker, the absorbance obtained from the chromogenic assay of a substrate is measured. A radioisotope is also used as a detectable marker by measuring the radiation dose. The results thus detected may be imaged using suitable image methods.

Step 4) is directed to attaching a peptide that will serve as a label onto the surface of the liposomes. An IL-4 receptor-targeting peptide (IL4RPep) having the amino acid sequence of SEQ ID NO: 1 (CRKRLDRNC) is conjugated at a molar ratio of 1:1~3 with maleimide-modified $DSPE-PEG_{2000}$ ($DSPE-PEG_{2000}$-maleimide). Then, the resulting $DSPE-PEG_{2000}$-IL4RPep is reacted at 50~70° C. for 1~3 hours with the anticancer agent-loaded liposomes labeled with the marker so that it is secondarily inserted into the liposomes. The IL4RPep peptide is present in an amount of 0.1~5 mol % based on total moles of lipid in the liposomes, and preferably in an amount of 0.1~3 mol %.

In a preferred embodiment of the present invention, the surfaces of the liposomes or lipids on the surface thus prepared are labeled with both the IL4RPep peptide and the markers, and they are then loaded with an anticancer agent.

When the IL4RPep-labeled liposomes are applied to encephaloma cells (C6, GBM8401), weak fluorescence is observed in C6 cells almost no IL-4 receptors are present thereon, whereas strong fluorescence is observed in GBM8401 cells, with an abundance of IL-4 receptors thereon. Accordingly, the expression patterns of IL-4 receptors of cancer cells differ from one kind to another.

In the GBM8401 cells treated with the IL4RPep-labeled liposomes of the present invention, strong red fluorescence is observed. Particularly, the liposomes labeled with 3 mol % of IL4RPep are found to mainly bind in abundance to encephaloma cells whereas weak fluorescence is detected in C6 cells, indicating that almost no IL4RPep is bound to the cells.

Strong red fluorescence is observed within GBM8401 cells treated with the IL4RPep-labeled liposomes of the present invention. Much fluorescence is present particularly in the cell center, demonstrating the influx of many liposomes into cells. Best in vivo targeting is conducted with the liposomes labeled with 1.5 mol % of IL4RPep, with maximal fluorescence signals detected 48 hours after in vivo introduction of the liposomes.

Significant suppression of tumor growth is observed in nude mice heterotransplanted with encephaloma cells (GBM8401) when the IL4RPep-labeled liposomes (IL4RPep-Lipo-Dox) of the present invention are administered to the mice, compared to the administration of liposomes (Lipo-Dox) that are not labeled with IL4RPep.

When the IL4RPep-labeled liposomes are applied to lung cancer cells (H226, H460), strong fluorescence is observed in H226 cells which have an abundance of IL-4 receptors, whereas weak fluorescence is observed in H460 cells, which have almost no IL-4 receptors. Accordingly, the expression patterns of IL-4 receptors of cancer cells differ from one kind to another.

In the H226 cells treated with the IL4RPep-labeled liposomes of the present invention, strong red fluorescence is observed, indicating that lots of IL4RPep bind to and are introduced into the cells. In contrast, almost no IL4RPep binds to nor is introduced into H460 cells as only weak fluorescence is detected from the cells.

Further, much stronger red fluorescence attributed to the anticancer agent is observed in the H226 cells treated with IL4RPep of the present invention (IL4RPep-Lipo-Dox) than liposomes which are not labeled with IL4RPep (Lipo-Dox). On the other hand, weak fluorescence is detected in H460 cells when they are treated with liposomes whether labeled (IL4RPep-Lipo-Dox) or not (Lipo-Dox).

In lung cancer cell tissues (H226), strong red fluorescence signals are observed when liposomes are labeled with both L4RPep and Cy5.5 (red fluorescence) [IL4RPep-Lipo-Cy5.5] while almost none of red fluorescence signals are detected when liposomes are labeled with Cy5.5 (red fluorescence) but not with IL4RPep [Lipo-Cy5.5]. In addition, a number of IL4RPep-labeled liposomes [IL4RPep-Lipo-Cy5.5] are arranged in and around tumor vessels.

In nude mice heterotransplanted with lung cancer cells (H226), the administration of the IL4RPep-labeled liposomes (IL4RPep-Lipo-Dox) of the present invention induces significantly higher inhibitory effects on tumor growth and stronger red fluorescence signals attributable to doxorubicin than does the administration of the liposomes that are not labeled with IL4RPep (Lipo-Dox) or the administration of the anticancer agent (Dox) itself. Therefore, the amount of doxorubicin (red fluorescence) delivered to tumor tissues is closely correlated with the inhibitory activity of the liposomes against tumor growth.

Thanks to IL4RPep that specifically binds to the IL-4 receptor, as described above, the anticancer agent-loaded liposomes labeled with IL4RPep in accordance with the present invention can deliver the drug selectively to cancer cells in which the IL-4 receptor is overexpressed. This selective drug delivery results from the specific recognition of cancer cells by the peptide. Therefore, IL4RPep can increase the pharmaceutical efficacy of the drug only in cancerous tissue, with a concomitant significant decrease in side effects in normal tissues, and makes in vivo imaging and the early diagnosis of tumors possible. Therefore, the anticancer agent-loaded liposomes labeled with IL4RPep in accordance with the present invention can be used effectively in a target-aiming drug delivery system for the diagnosis or treatment of cancer.

For administration, the liposomes according to the present invention may further comprise one or more pharmaceutically acceptable carriers therein. The pharmaceutically acceptable carrier useful in the present invention may be selected from saline, sterile water, Ringer's solution, buffered saline, dextrose solution, maltodextrin solution, glycerol, ethanol and a combination thereof. Optionally, a typical additive such as an antioxidant agent, a buffer, a bactriostatic agent, etc. may be added. The drug delivery system may be in the form of injections such as suspensions or emulsions, pills, capsules, granules or tablets by formulating the liposomes with a diluent, a dispersant, a surfactant, a binder and a lubricant. Further, the liposomes may be formulated into desirable dosage forms according to either the disease or the drug using a suitable method known in the art or disclosed in Remington's Pharmaceutical Science (latest), Mack Publishing Company, Easton Pa.

Depending on purpose, the liposomes according to the present invention may be administered orally or parenterally (e.g., intravenously, subcutaneously, intraperitoneally, or topically). The dose of the liposomes may vary depending on various factors including the weight, age, gender, and the state of health of the patients as well as on the diet, the time of administration, the route of administration, the rate of excrement, and the severity of illness. Preferably, the anticancer agent loaded into the liposomes is administered at a dose of about 0.1~5 mg/kg weight (or 10~100 mg/m² body surface area) once a week for 3~4 weeks.

Mode for Invention

A better understanding of the present invention may be obtained through the following examples which are set forth to illustrate, but are not to be construed as limiting the present invention.

EXAMPLE 1

Preparation of Doxorubicin-Loaded Liposomes Labeled with IL-4 Receptor-Targeting Peptide and Near-Infrared Fluorochrome Cholesterols, L-α-phosphatidylcholine (PC), 1,2-diacyl-sn-glycero-3 -phosphoethanolamine-N-[methoxy(polyethylene glycol)-2000] (DSPE-PEG$_{2000}$), 1,2-distearoyl-sn-glycero-3-phosphoethanolamine-N-[maleimide (polyethyleneglycol)-2000] and DSPE-PEG$_{2000}$-maleimide used in this Example were purchased from Avanti Polar Lipids.

1. Preparation of Liposomes

Liposomes were prepared using a solvent-injection and extrusion method. First, all lipids (PC, cholesterol, DSPE-PEG$_{2000}$) were dissolved at a molar ratio of 6:4:0.5 in ethanol at 60° C. The lipid mixture was hydrated at a volume ratio of 1:10 with water for 1 hour at 60° C. The hydrated lipid mixture was forced to pass six times through polycarbonate membrane filters with a pore size of 0.2 μm and then six times through filters with a pore size of 0.05 μm to yield liposomes homogeneous in size. The dimension of the liposomes was determined using a dynamic light scattering method (DLS). They ranged in diameter from 80 to 120 nm.

2. Loading of Drug into Liposomes

The anticancer agent doxorubicin was loaded into liposomes by a remote-loading method using ammonium sulfate (($NH_4$)$_2SO_4$). In this regard, 250 mM ($NH_4$)$_2SO_4$, which is the water phase in the solution in which the liposome is present, was excluded. Then, the water phase-excluded liposomes were placed within a dialysis membrane (molecular weight 3 k) in a sufficient amount of 10% sucrose solution containing 5 mM NaCl to remove ammonium sulfate from the surface of the liposomes. Then, a doxorubicin HCl solution was added to the liposome solution and reacted at 50~70° C. for 1~3 hours, followed by rapid chilling to impregnate the liposomes with doxorubicin. The concentration of doxorubicin within the liposomes was on the order of 1.5~2 mg/mL.

3. Labeling of Fluorescent into Liposomes

Liposomes were labeled with Cy™5.5 amidite or rhodamine-phosphatidylethanolamine (rhodamine-PE; red fluorescence). In this regard, the fluorescent was mixed with all lipids in ethanol and then injected into phosphate buffered saline (PBS). Due to its hydrophobicity, the fluorescent was entrapped within the lipid bilayer.

4. Preparation of Doxorubicin-Loaded Liposomes Labeled with IL-4 Receptor-Targeting Peptide and Fluorescent Liposomes labeled with peptides were constructed using a post-insertion method. IL4RPep (the amino acid sequence of CRKRLDRNC, SEQ ID NO:1) was conjugated at a ratio of 1:2 with maleimide-modified DSPE-PEG$_{2000}$ (DSPE-PEG$_{2000}$-maleimide). Subsequently, DSPE-PEG$_{2000}$-IL4RPep was secondarily inserted into the liposomes by incubation at 60° C. for 1 hour with the doxorubicin-loaded liposomes labeled with a fluorescent compound. In this context, the peptide was present in an amount of 0~3 mol % based on total moles of lipid in the liposomes.

EXPERIMENTAL EXAMPLE 1

Immunofluorescence Assay for Expression of IL-4 Receptor on Encephaloma Cell

Encephaloma cells (C6 and GBM8401) were seeded at a density of 5×10$^4$ cells/well into respective culture dishes and incubated overnight. The cells were fixed at −20° C. for 5 min with methanol and then reacted at room temperature for 1 hour with an FITC (green fluorescence)-conjugated antibody to the IL-4 receptor. Observation of fluorescent signals under a fluorescence microscope determined the expression levels of the IL-4 receptor.

Figure 1:
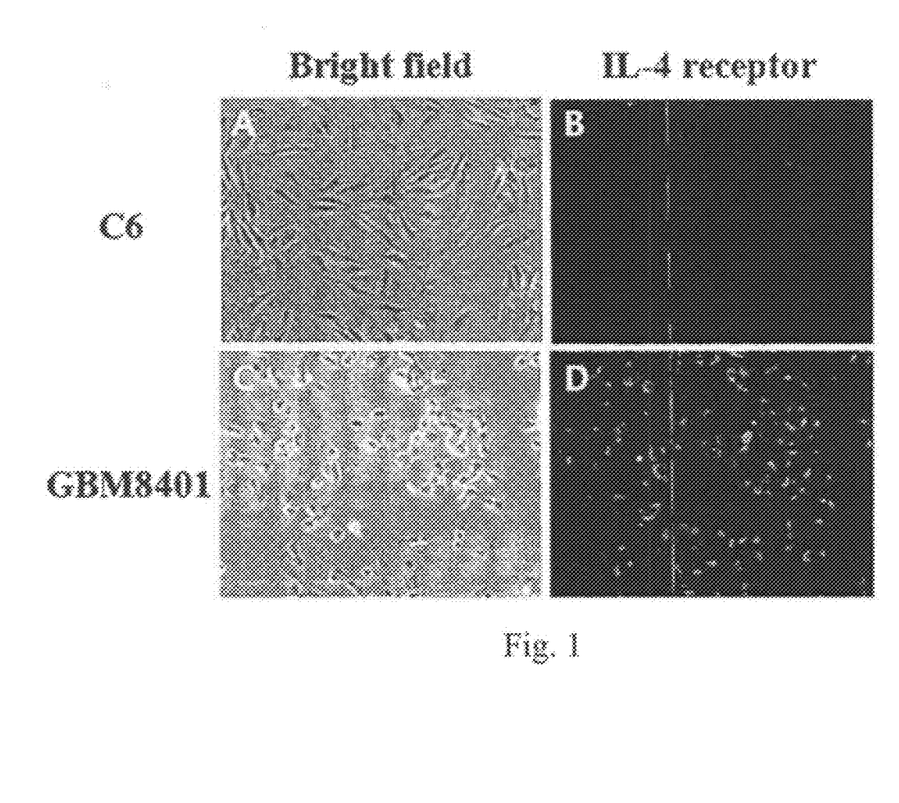
FIG. 1 shows expression levels of the IL-4 receptor in encephaloma cells (C6 and GBM8401) as observed by fluorescence microscopy.

The results are shown in FIG. 1.

As shown in FIG. 1, weak fluorescence was detected in C6 cells, with near absence of the IL-4 receptor whereas GBM8401 cells were observed to have strong fluorescence, with the presence of abundant IL-4 receptors.

EXPERIMENTAL EXAMPLE 2

Binding of IL4RPep-Labeled Liposomes to Encephaloma Cells

Liposomes labeled with polyethylene glycol, a fluorescent (1 mol % rhodamine-PE, red fluorescence) and IL4RPep (0~3 mol %) on their surfaces were prepared as described in Example 1. Encephaloma cells (C6 and GBM8401) were cultured and then incubated at 4° C. for 1 hour with the liposomes labeled with both IL4RPep (0 mol %, 0.75 mol %, 1.5 mol % or 3 mol %) and rhodamine-PE (1 mol %, red fluorescence). Then, the cells were washed and observed under a fluorescence microscope to examine the binding of IL4RPep onto the surface of the cells.

Figure 2:
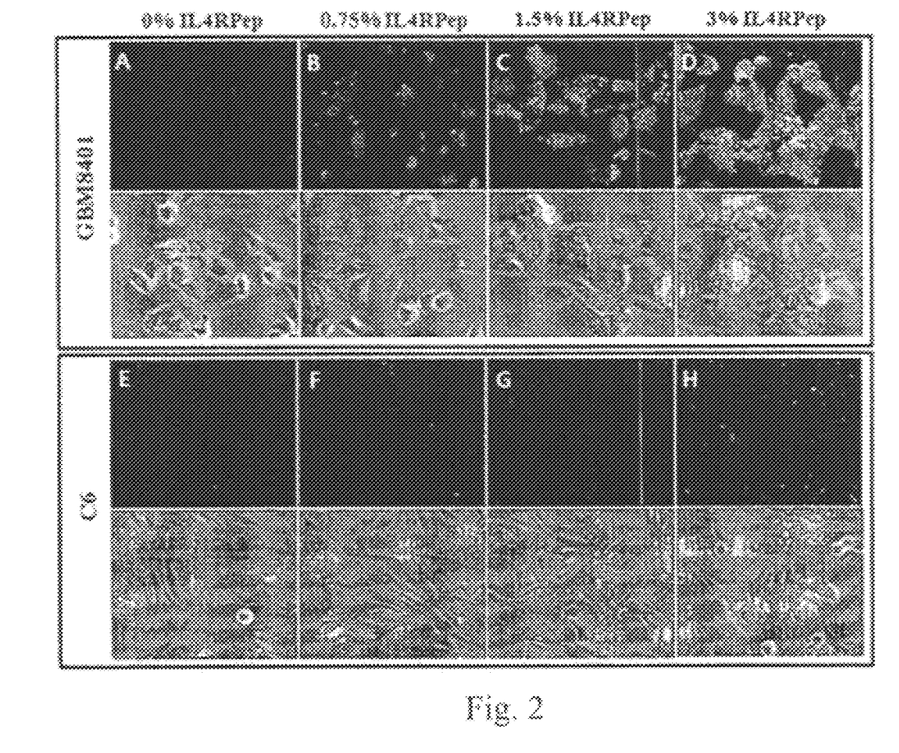
FIG. 2 shows the binding of the liposomes labeled with both IL4RPep (0 mol %, 0.75 mol %, 1.5 mol % and 3 mol %) and rhodamine-PE (red fluorescence) to encephaloma cells (C6 and GBM8401) as observed by fluorescence microscopy.

The results are shown in FIG. 2.

As shown in FIG. 2, when the IL4RPep-labeled liposomes of the present invention were applied thereto, GBM8401 cells were observed to exhibit strong red fluorescence signals, indicating that IL4RPep was strongly bound to the surface of the cells. Particularly, the liposomes labeled with 3 mol % of IL4RPep were found to bind to the encephaloma cells to the highest extent. In contrast, a weak fluorescence signal was observed in the C6 cells to which the IL4RPep-labeled liposomes were applied, indicating that almost no IL4RPep was bound to the cells.

EXPERIMENTAL EXAMPLE 3

Introduction of IL4RPep-Labeled Liposomes into Encephaloma Cell (GBM8401)

Encephaloma cells (GBM8401) were seeded at a density of 5×10$^4$ cells/well into plates and then incubated at 37° C. for 1 hour with the liposomes, prepared in Experimental Example 2, which were labeled with both 3 mol % of IL4RPep and 1 mol % of rhodamine-PE (red fluorescence). Subsequently, confocal tomography was performed at regular intervals of approximately 1 μm to examine intracellular fluorescence.

Figure 3:
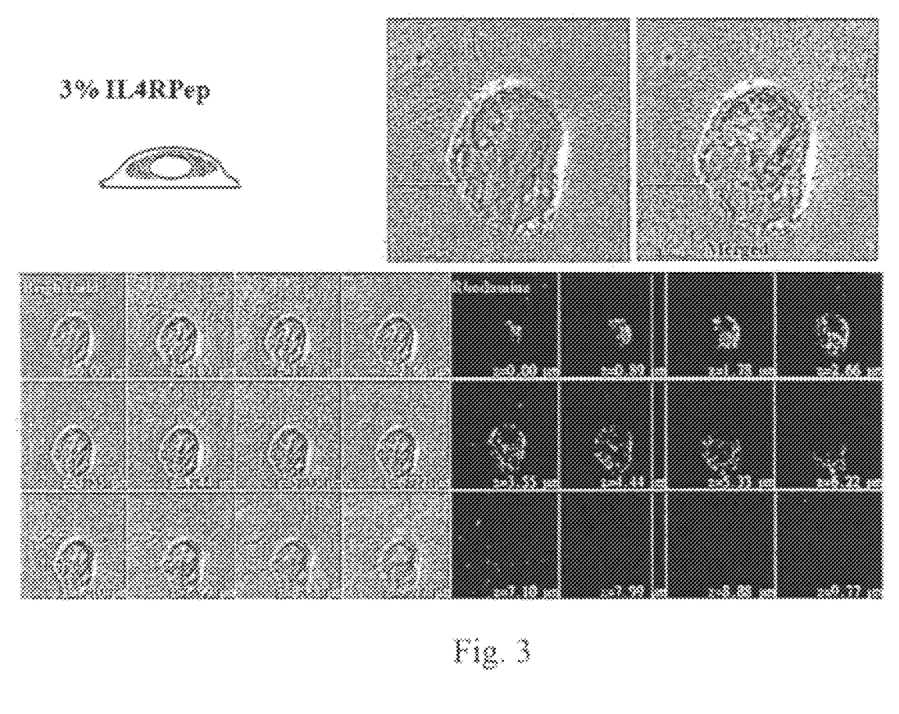
FIG. 3 shows the introduction of the liposomes labeled with both IL4RPep (3 mol %) and rhodamine-PE (red fluorescence) into encephaloma cells (GBM8401) as observed by confocal tomography.

The results are shown in FIG. 3.

As can be seen in FIG. 3, strong red fluorescence was observed in the inside of the GBM8401 cells treated with the IL4RPep-labeled liposomes of the present invention. Particularly, abundant red fluorescence was found even in the cell center 5 μm distant from the cell surface, implying the active intracellular introduction of the liposomes.

EXPERIMENTAL EXAMPLE 4

In vivo Fluorescence Imaging of IL4RPep-Labeled Liposomes on Encephaloma Target

All animal tests were performed according to the guidelines of the Institutional Animal Care and Use Committee. Experimental animals were transplanted with a tumor xenograft. For this, a suspension of the luciferase-expressing encephaloma cell line (GBM8401, 1×10$^7$ cells) in a medium was implanted in the brain tissue of six-week-old BALB/c male severe combined immune deficiency (SCID) mice after the skulls were pierced. For three weeks, the tumor cells were grown to a size of 0.5~1 cm. Thereafter, the liposomes labeled with both IL4RPep (0 mol %, 0.25 mol %, 0.75 mol %, 1.5 mol % or 3 mol %) and rhodamine-PE (1 mol %, red fluorescence), prepared in Experimental Example 2, were injected into the mice via the tail vein. The brain tumor targets were monitored by taking in vivo fluorescence images 24, 48, 72 and 144 hours after the injection.

Figure 4:
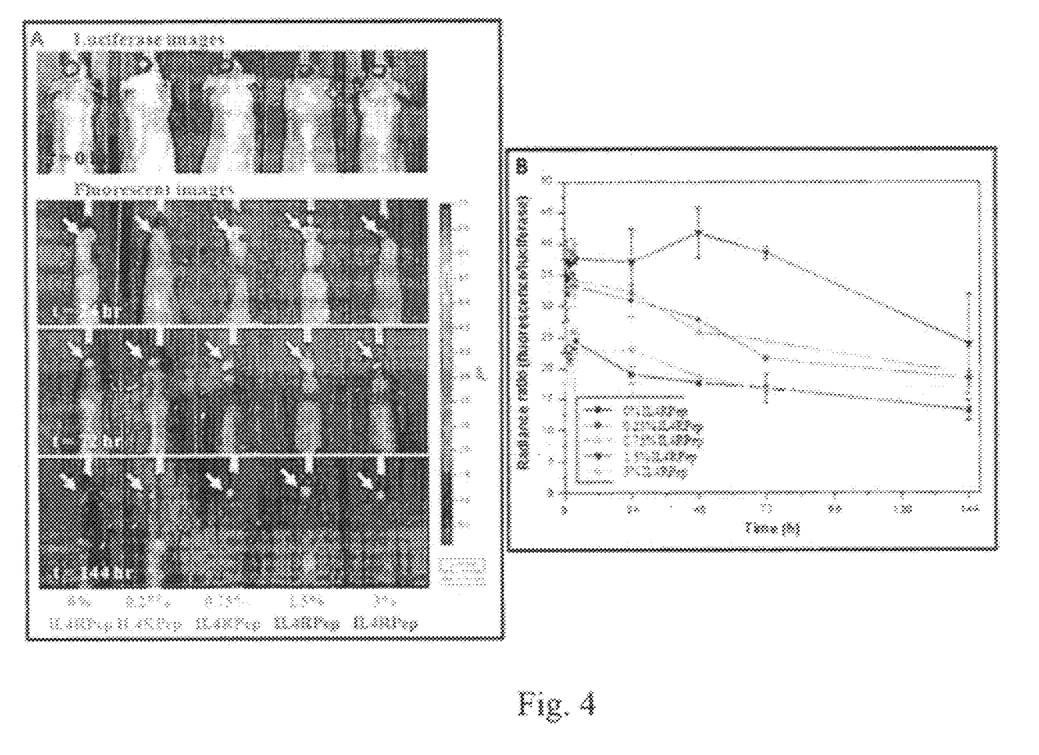
FIG. 4 shows (A) in vivo fluorescence images of brain tumor targets over time (24 hrs, 48 hrs, 72 hrs and 144 hrs) after the liposomes labeled with both IL4RPep (0 mol %, 0.25 mol %, 0.75 mol %, 1.5 mol % and 3 mol %) and rhodamine-PE (1 mol %, red fluorescence) are injected into brain tumor cell line (GBM8401)-transplanted SCID mice via the tail vein and (B) quantified results of the fluorescence.

The results are shown in FIG. 4.

As can be seen in FIG. 4, fluorescence was observed from 24 hours after the injection of the liposomes labeled with both IL4RPep (0 mol %, 0.25 mol %, 0.75 mol %, 1.5 mol % or 3 mol %) and rhodamine-PE (1 mol %, red fluorescence) via the mouse tail vein and continued until 144 hours after the injection (A). In contrast to the in vitro experiment in which the maximum binding to the cultured cells (GBM8401) was obtained with the liposomes labeled with 3 mol % of IL4RPep, the in vivo experiment showed the superiority of the liposomes labeled with 1.5 mol % of IL4RPep to target other liposomes, with the appearance of maximal fluorescence signals 48 hours after the injection.

EXPERIMENTAL EXAMPLE 5

IL4RPep-Mediated Selective Drug Delivery of Doxorubicin-Loaded Liposomes to Brain Tumor and Target Therapy To evaluate the IL4RPep-mediated selective drug delivery of the doxorubicin-loaded liposomes to brain tumors, the following experiment was conducted.

The encephaloma cell line (GBM8401, 1×10$^7$ cells) transformed with a luciferase gene was transplanted into the brain tissue of nude mice. The liposomes prepared in Example 1 were injected at a dose of 4 mg/kg into the tail vein on 6, 9 and 13 days after the tumor transplantation (three injections in total). The total flux of luminescence of the luciferase, that is, the number of photons excited per second (photons/s) were measured for 16 days to monitor the size of the tumors.

Figure 5:
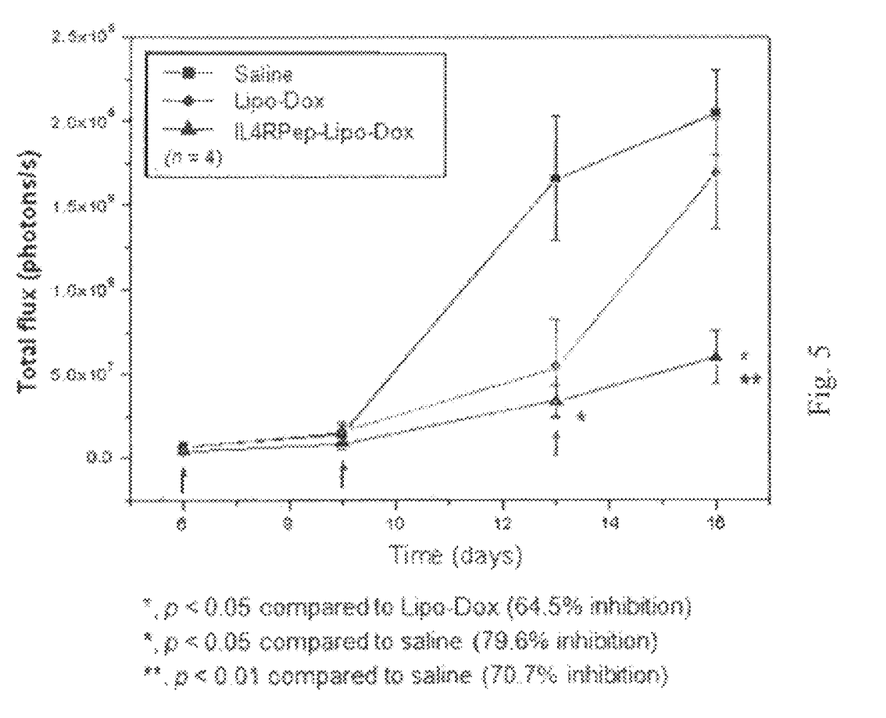
FIG. 5 is a graph showing a change of tumor size with time after the liposomes labeled with IL4RPep (IL4RPep-Lipo-Dox) were injected into nude mice into which brain tumor cells transformed with a luciferase gene were previously heterotransplanted.

The results are shown in FIG. 5.

When administered to the nude mice transplanted with a tumor xenograft, as can be seen in FIG. 5, IL4RPep-labeled liposomes (IL4RPep-Lipo-Dox) were found to further suppress the size of tumors by 65%, compared to the liposomes not labeled with IL4RPep (Lipo-Dox), and by 70% or greater compared to saline, with statistical significance.

EXPERIMENTAL EXAMPLE 6

Immunofluorescence Assay of IL-4 Receptor on Lung Cancer Cells

Lung cancer cells (H226 and H460) were cultured and then incubated at room temperature for 1 hour with an antibody to the IL-4 receptor. After the reaction of a rhodamine (red fluorescence)-conjugated secondary antibody, nuclei of the cells were stained with DAPI (4',6-diamidino-2-phenylindole). Using fluorescence microcopy, the expression levels of the IL-4 receptor were determined.

Figure 6:
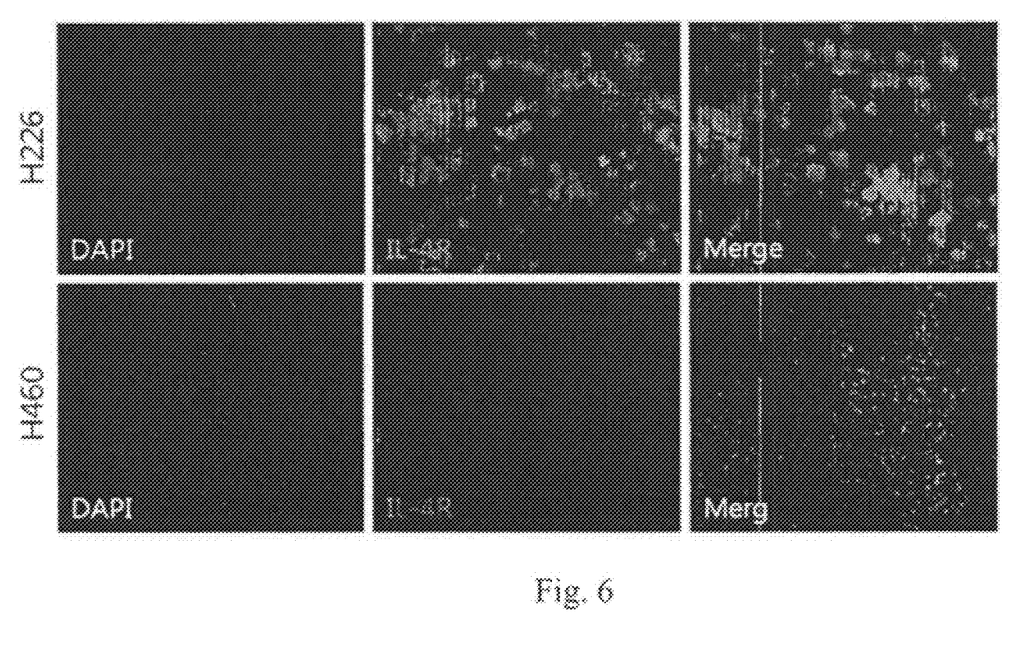
FIG. 6 shows the expression levels of IL-4 receptors in lung cancer cells (H226 and H460) as observed by fluorescence microscopy.

The results are shown in FIG. 6.

As can be seen in FIG. 6, strong fluorescence was observed in H226 cells, which have a high expression level of IL-4 receptors, whereas weak fluorescence was detected in H460 cells, showing that there was no expression of the IL-4 receptor thereon.

EXPERIMENTAL EXAMPLE 7

Binding of IL4RPep-Labeled Liposome to Lung Cancer Cell and Intracellular Introduction Lung cancer cells (H226 and H460) were cultured and incubated at 4° C. and 37° C. for 1 hours with liposomes labeled with both IL4RPep (1.5 mol %) and Cy5.5 (red fluorescence). The cells were washed and the nucleus stained with DAPI. Fluorescence signals were observed under a fluorescence microscope to examine the binding of the peptide to the cells and the intracellular introduction of the peptide.

Figure 7:
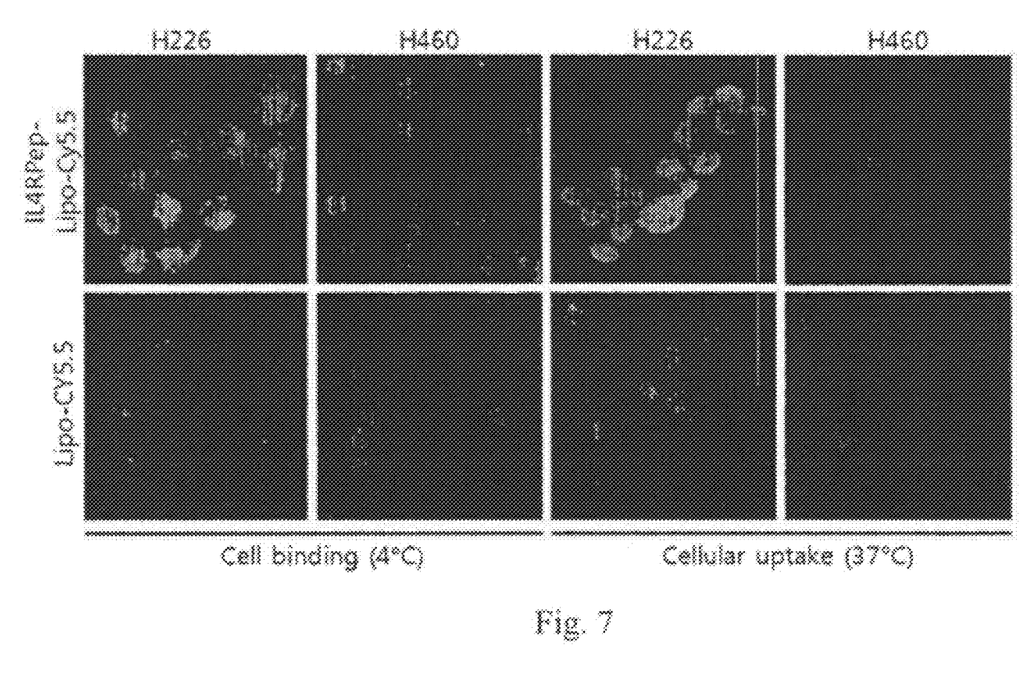
FIG. 7 shows the binding and intracellular introduction of the liposomes labeled with both IL4RPep (1.5 mol %) and Cy5.5 (red fluorescence) to lung cancer cells (H226 and H460) as observed by fluorescence microscopy.

The results are shown in FIG. 7.

As shown in FIG. 7, H226 cells were observe to exhibit strong red fluorescence signals, indicating that IL4RPep was strongly bound to the surface of the cells. In contrast, a weak fluorescence signal was observed in the H460 cells, indicating that IL4RPep had neither bound to the cells nor been introduced into the cells.

EXPERIMENTAL EXAMPLE 8

IL4RPep-Mediated Selective Drug Delivery of Doxorubicin-Loaded Liposome to Lung Cancer Cells Lung cancer cells (H226 and H460) were cultured and incubated at 37° C. for 1 hour with the liposomes prepared in Example 1 [doxorubicin-loaded liposomes labeled with both IL4RPep (1.5 mol %) and Cy5.5 (red fluorescence)]. The cells were washed and nucleus stained with DAPI. The fluorescence (red) of the doxorubicin itself was observed using a fluorescence microscope to examine drug delivery into the inside of the cells.

Figure 8:
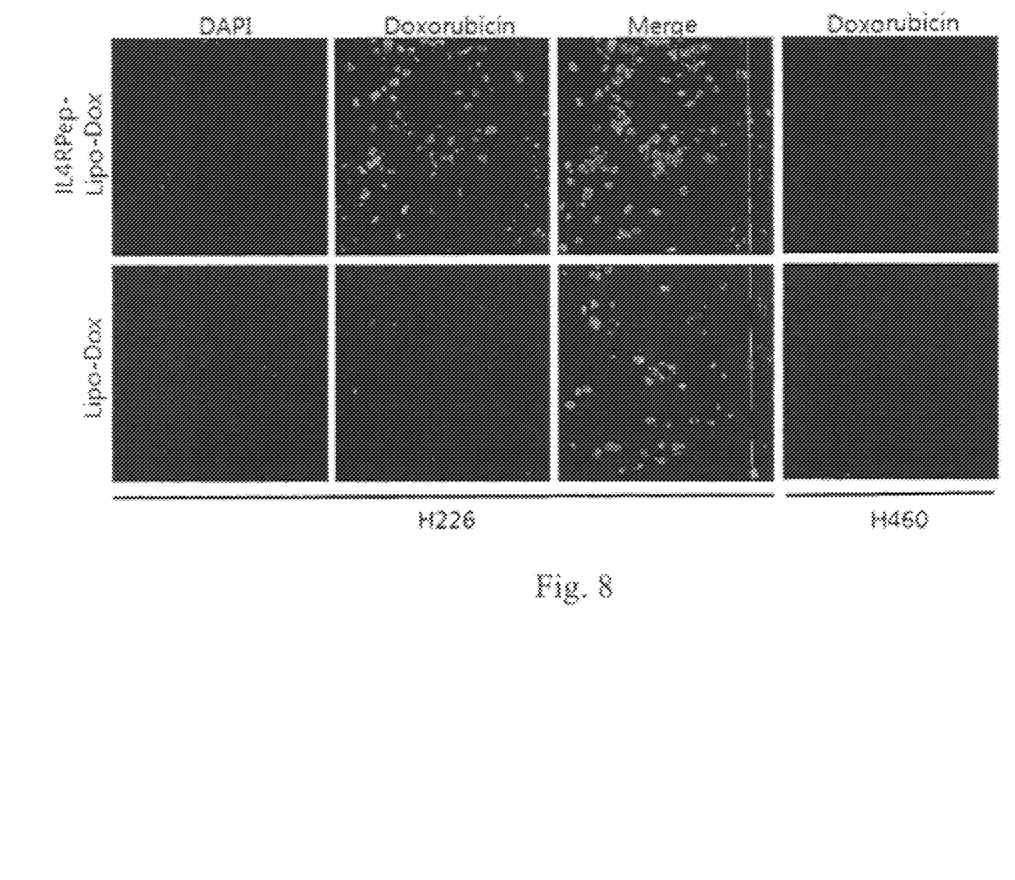
FIG. 8 shows the degrees of drug delivery into lung cancer cells (H226 and H460) by the liposomes labeled with IL4RPep (IL4RPep-Lipo-Dox) as measured by fluorescence microscopy using the (red) fluorescence of doxorubicin itself.

The results are shown in FIG. 8.

As can be seen in FIG. 8, a higher level of doxorubicin red fluorescence was observed in H226 cells when they were treated with the IL4RPep-labeled liposomes (IL4RPep-Lipo-Dox) than the liposomes not labeled with IL4RPep (Lipo-Dox). In contrast, weak fluorescence was detected in H460 cells whether they were incubated with IL4RPep-labeled liposomes (IL4RPep-Lipo-Dox) or with liposomes not labeled with IL4RPep (Lipo-Dox).

EXPERIMENTAL EXAMPLE 9

IL4RPep-Labeled Liposomes Targeting Lung Cancer Cells In vivo

In order to form a tumor xenograft in experimental animals, human lung cancer cells cultured in RPMI-1640 (H226, $1 \times 10^7$ cells) were subcutaneously injected into the right upper limb or hind limb of six-week-old BALB/c male nude mice (HyoChang Science).

The tumor cells were allowed to grow to a size of 0.5~1 cm. Then, liposomes labeled with both IL4RPep and Cy5.5 (red fluorescence) was injected at a dose of 5 mg/kg into the mice via the tail vein. After circulation for 2 hours, the tumor tissues were excised, cryosectioned and observed under a fluorescence microscope. On the other hand, the tumor tissues were stained (green fluorescent) using an antibody to CD31, a vascular biomarker and observed under a fluorescence microscope at a high magnification. The lung cancer cell line (H226) used in this experiment was cultured in RPMI-1640 supplemented with antibiotics (penicillin and streptomycin) and 10% FBS (fetal bovine serum), with passage every 3~4 days.

Figure 9:
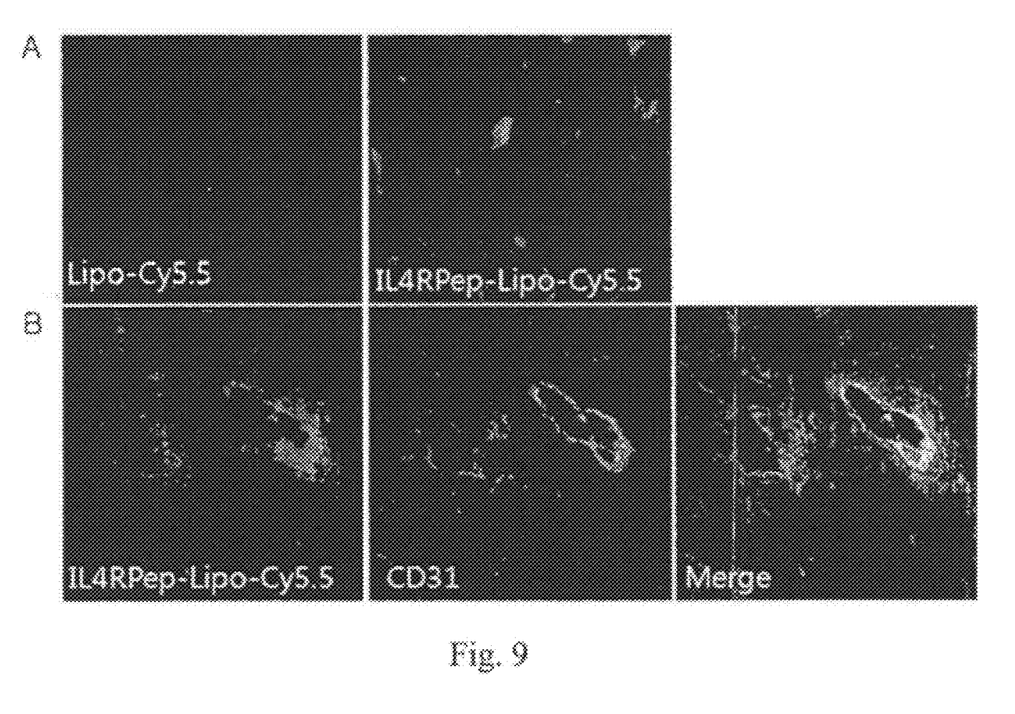
FIG. 9 shows (A) the liposomes labeled with IL4RPep (IL4RPep-Lipo-Cy5.5) in tumor tissues after the intravenous injection of the liposomes into nude mice which were previously heterotransplanted with lung cancer cells, as observed by fluorescence microscopy and (B) the tumor tissues after they were stained (green fluorescent) using an antibody to the vascular biomarker CD31, as observed at high magnification by fluorescence microscopy.

The results are shown in FIG. 9.

As can be seen in FIG. 9, high levels of red fluorescence were observed in the lung cancer cell (H226) tissues to which the liposomes labeled with both IL4RPep and Cy5.5 (red fluorescence) [IL4RPep-Lipo-Cy5.5] were applied whereas almost no red fluorescence was detected when liposomes labeled with Cy5.5 (red fluorescence), but not with IL4RPep, were used (A). In addition, a number of IL4RPep-labeled liposomes [IL4RPep-Lipo-Cy5.5] were found in the tumor vessels and the area around the tumor (B).

EXPERIMENTAL EXAMPLE 10

IL4RPep-Mediated Selective Drug Delivery of Doxorubicin-Loaded Liposomes to Lung Cancer and Target Therapy To evaluate the IL4RPep-mediated selective drug delivery of the doxorubicin-loaded liposomes to lung cancer, the following experiment was conducted.

The lung cancer cell line (H226, $1 \times 10^7$ cells) was transplanted into the right upper limb or hind limb of nude mice. When the tumor grew to a diameter of 3 mm, the liposomal solution prepared in Example 1 was injected into the mice via the tail vein in such an amount that doxorubicin was administered at a dose of 1 mg/kg (seven times in total, twice a week). Tumor sizes were monitored for 24 days. The tumor size (mm$^3$) was calculated according to the formula long axis×short axis×short axis×0.52. On day 24 after the injection, the tumors were excised and cryosectioned. The level of doxorubicin in the tumor tissue was determined by observing the inherent red fluorescence of doxorubicin.

Figure 10:
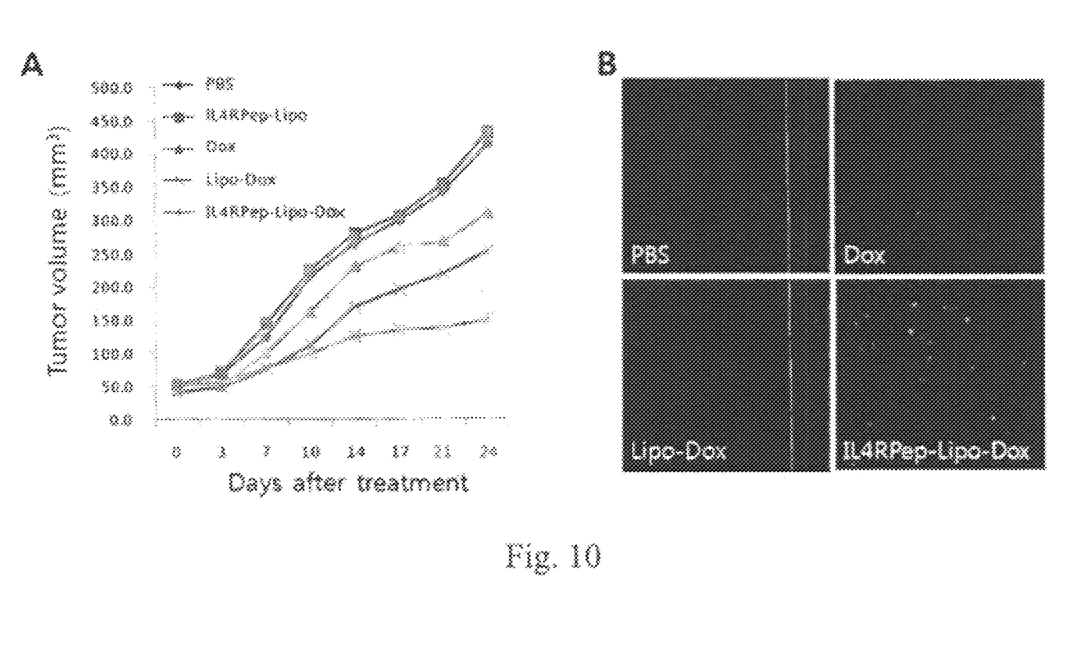
FIG. 10 shows (A) the sizes of tumors over time after administration of the liposomes labeled with IL4RPep (IL4RPep-Lipo-Dox) to nude mice which had previously been heterotransplanted with lung cancer cells and (B) the contents of doxorubicin within the tumor tissues as observed by fluorescence microscopy using the (red) fluorescence of doxorubicin itself.

The results are shown in FIG. 10.

When administered to the nude mice transplanted with a lung cancer xenograft, as can be seen in FIG. 10, IL4RPep-labeled liposomes (IL4RPep-Lipo-Dox) were found to inhibit the growth of tumors at significantly higher efficiency, compared to the liposomes not labeled with IL4RPep (Lipo-Dox), or doxorubicin alone (A). In addition, a much higher level of red fluorescence, attributed to doxorubicin, was observed in the tumor tissues administered with the IL4RPep-labeled liposomes (IL4RPep-Lipo-Dox), indicating that the quantity of the doxorubicin (red fluorescence) delivered to the tumor tissue was closely correlated with the inhibitory effect of the IL4RPep-labeled liposomes on tumor growth.

INDUSTRIAL APPLICABILITY

As described hitherto, the anticancer agent-loaded liposomes labeled with IL4RPep in accordance with the present invention can deliver the drug selectively to cancer cells on which the IL-4 receptor is overexpressed, thanks to the ability of IL4RPep to specifically recognize the IL-4 receptor. This drug delivery enables the anticancer drug to selectively attack cancer cells. Accordingly, the IL4RPep can increase pharmaceutical efficacy only on cancer tissues, with the concomitant decrease of side effects on normal tissues, and allows the in vivo imaging and early diagnosis of tumors. Hence, the anticancer agent-loaded liposomes labeled with IL4RPep in accordance with the present invention can be effectively used in a target-aiming drug delivery system for the diagnosis or treatment of cancer.

a cholesterol, and
wherein the first lipid amounts to 60~70 mol % of total lipids in the liposome, the second lipid amounts to 1~10 mol % of total lipids in the liposome, and the cholesterol amounts to 1~40 mol % of total lipids in the liposome.

2. The target-aiming drug delivery composition of claim 1, wherein the anticancer agent is doxorubicin.

3. A method for manufacturing a target-aiming drug delivery composition consisting of:
   1) dissolving a first lipid, a second lipid and a cholesterol in ethanol to assure a lipid mixture, hydrating the mixture in water to form a lipid suspension, and forcing the lipid suspension through a filter to yield homogeneous liposomes,
   2) adding an anticancer agent to the liposomes formed in step 1) to afford anticancer agent-loaded liposomes,
   3) labeling the anticancer agent-loaded liposomes with at least one marker, and
   4) conjugating a peptide targeting interleukin-4 receptor (IL4RPep) consisting of the amino acid sequence of SEQ ID NO: 1 to maleimide-modified DSPE-PEG$_{2000}$ (DSPE-PEG$_{2000}$-maleimide) and
   5) incubating at 50-70° C. for 1-3 hours the conjugate with the anticancer agent-loaded liposome labeled with the marker to insert the IL4RPep into the surface of the liposomes; and
   wherein the first lipid, the second lipid and the cholesterol are mixed at a molar ratio of 60~70:1~10:1~40 in step 1).

4. The method of claim 3, wherein the anticancer agent loaded within the liposomes in step 2) is present at a concentration of 1 to 5 mg per mL of the liposome.

The invention claimed is:

1. A target-aiming drug delivery composition consisting of as an active ingredient an anticancer agent-loaded liposome that is labeled with a peptide targeting interleukin-4 receptor consisting of the amino acid sequence of SEQ ID NO: 1 conjugated to a maleimide-modified DSPE-PEG$_{2000}$ (DSPE-PEG$_{2000}$-maleimide), wherein the peptide is present in an amount of 0.1 to 3 mol %, based on total moles of lipids in the liposome,
   wherein the liposome is a multilamellar liposome consisting of:
   a first lipid selected from the group consisting of phosphatidyl choline (PC), phosphatidyl glycerol (PG), phosphatidyl serine (PS) and phosphatidyl ethanolamine (PE);
   a second lipid, wherein the second lipid is distearoyl-phosphatidylethanolamine-polyethylenoglycol (DSPE-PEG); and 5. The method of claim 3, wherein the at least one marker in step 3) is selected from the group consisting of a radioisotope, a chromophore, a luminescent, a fluorescent, a superparamagnetic particle, an ultrasmall paramagnetic particle, and a chromogenic enzyme.

6. The method of claim 3, wherein the IL4RPep is conjugated at a molar ratio of 1:1 to 1:3 with the maleimidemodified DSPE-PEG$_{2000}$ (DSPE-PEG$_{2000}$-maleimide) in step 3.

7. The target-aiming drug delivery composition of claim 1,
   further comprising at least one marker selected from the group consisting of a radioisotope, a chromophore, a luminescent, a fluorescent, a superparamagnetic particle, an ultrasmall paramagnetic particle, and a chromogenic enzyme.

* * * * *

```
SEQUENCE LISTING

<160> NUMBER OF SEQ ID NOS: 1

<210> SEQ ID NO 1
<211> LENGTH: 9
<212> TYPE: PRT
<213> ORGANISM: Artificial Sequence
<220> FEATURE:
<223> OTHER INFORMATION: amino acid sequence of interlukin-4 receptor

<400> SEQUENCE: 1

Cys Arg Lys Arg Leu Asp Arg Asn Cys
1               5
```